United States Patent
Maffia

(10) Patent No.: US 9,359,409 B2
(45) Date of Patent: Jun. 7, 2016

(54) ANTIMICROBIAL PEPTIDES, COMPOSITIONS COMPRISING THE SAME AND USES THEREOF

(71) Applicants: CONSEJO NACIONAL DE INVESTIGACIONES CIENTIFICAS Y TECNICAS, Buenos Aires (AR); UNIVERSIDAD NACIONAL DE QUILMES, Buenos Aires (AR)

(72) Inventor: Paulo Maffia, Buenos Aires (AR)

(73) Assignees: CONSEJO NACIONAL DE INVESTIGACIONES CIENTIFICAS Y TECNICAS, Buenos Aires (AR); UNIVERSIDAD NACIONAL DE QUILMES, Buenos Aires (AR)

( * ) Notice: Subject to any disclaimer, the term of this patent is extended or adjusted under 35 U.S.C. 154(b) by 0 days.

(21) Appl. No.: 14/655,885

(22) PCT Filed: Dec. 26, 2013

(86) PCT No.: PCT/IB2013/061346
§ 371 (c)(1),
(2) Date: Jun. 26, 2015

(87) PCT Pub. No.: WO2014/106798
PCT Pub. Date: Jul. 10, 2014

(65) Prior Publication Data
US 2015/0344527 A1 Dec. 3, 2015

(30) Foreign Application Priority Data
Dec. 28, 2012 (AR) .............................. P20120105083

(51) Int. Cl.
*C07K 7/04* (2006.01)
*C07K 7/08* (2006.01)
*C07K 7/00* (2006.01)
*C07K 14/00* (2006.01)
*A61K 38/16* (2006.01)
*A61K 38/10* (2006.01)
*A61K 38/04* (2006.01)
*A61K 39/02* (2006.01)
*A61K 39/085* (2006.01)
*A61K 39/09* (2006.01)
*A61K 39/104* (2006.01)
*A61K 38/00* (2006.01)

(52) U.S. Cl.
CPC ............... *C07K 14/001* (2013.01); *A61K 39/02* (2013.01); *A61K 39/025* (2013.01); *A61K 39/085* (2013.01); *A61K 39/09* (2013.01); *A61K 39/104* (2013.01); *C07K 7/08* (2013.01); *A61K 38/00* (2013.01)

(58) Field of Classification Search
CPC ............... C07K 7/04; C07K 7/08; C07K 7/00; C07K 14/00; C07K 14/4723; A61K 38/1729; A61K 38/16; A61K 38/10; A61K 38/04
USPC ................... 514/1.1, 2.4, 2.7, 2.8, 21.3, 21.4; 530/324, 325, 326, 300
See application file for complete search history.

(56) References Cited

U.S. PATENT DOCUMENTS 6,696,238 B2    2/2004   Murphy et al.

OTHER PUBLICATIONS

Faccone et al, "ANtimicrobial activity of de novo designed cationic peptides against multi-resistant clinical isolates," European Journal of Medicinal Chemistry, 2014, 71: 31-35. Available online Nov. 1, 2013.*

* cited by examiner

*Primary Examiner* — Julie Ha
(74) *Attorney, Agent, or Firm* — Wenderoth, Lind & Ponack, L.L.P.

(57) ABSTRACT

Antimicrobial peptides set forth in SEQ ID Nos: 1-5 are described. The peptides have activity against Gram positive bacteria and against Gram negative bacteria. A bactericidal composition is also provided, which may comprise an amount between 0.5 µg/mL and 1024 µg/mL of the peptides and excipients.

8 Claims, 2 Drawing Sheets

ANTIMICROBIAL PEPTIDES, COMPOSITIONS COMPRISING THE SAME AND USES THEREOF

The present invention relates to antimicrobial peptides such as for example, the peptides shown in SEQ ID NO:1, SEQ ID NO:2, SEQ ID NO:3, SEQ ID NO:4 or SEQ ID NO:5. These peptides show activity against Gram positive bacteria and against Gram negative bacteria. It is also provided a bactericidal composition comprising an amount between 0.5 μg/ml and 1024 μg/ml of the peptides: and excipients.

BACKGROUND OF THE INVENTION

The treatment of chronic wounds and ulcers is complex and difficult and represents a challenge for the health system as a whole, having a strong impact on economy in general. In particular, the problem of recurrent infections with bacterial strains resistant to antimicrobial treatments.

Even though nowadays effective treatments are available for the majority of the infections, antibiotics abuse, carried out over many decades, has led to the generation of strains resistant to common-use antimicrobials by means of horizontal transfer of genes between pathogenic microorganisms.

This progressive decrease in the efficacy of first-choice antibiotics and the limited therapeutic approaches available for the wound treatment and healing, emphasize the need for new classes of drugs and their means of application.

Presently, some bactericidal peptides exist. Each peptide has different characteristics in terms of the minimum inhibitory concentrations that are to be used for achieving the desired bactericidal activity, in addition, they show differences in solubility, cytotoxicity, specificity and target against different pathogens.

Patent document U.S. Pat. No. 6,696,238 discloses polypeptides and defensins used as antimicrobials in the preparation of culture media.

BRIEF DESCRIPTION OF THE INVENTION

Antimicrobial peptides are provided, in a preferred embodiment the peptides may be those shown in SEQ ID NO:1, SEQ ID NO:2, SEQ ID NO:3, SEQ ID NO:4 or SEQ ID No:5. The peptides have activity against Gram positive bacteria and against Gram negative bacteria.

A bactericidal composition is provided, comprising an amount between 0.5 μg/mL and 1024 μg/mL of the peptides mentioned in the paragraph above; and excipients.

The use of the peptides 1 is provided for preparing a medicament for bacterial infections.

DETAILED DESCRIPTION OF THE INVENTION

Figure 1:
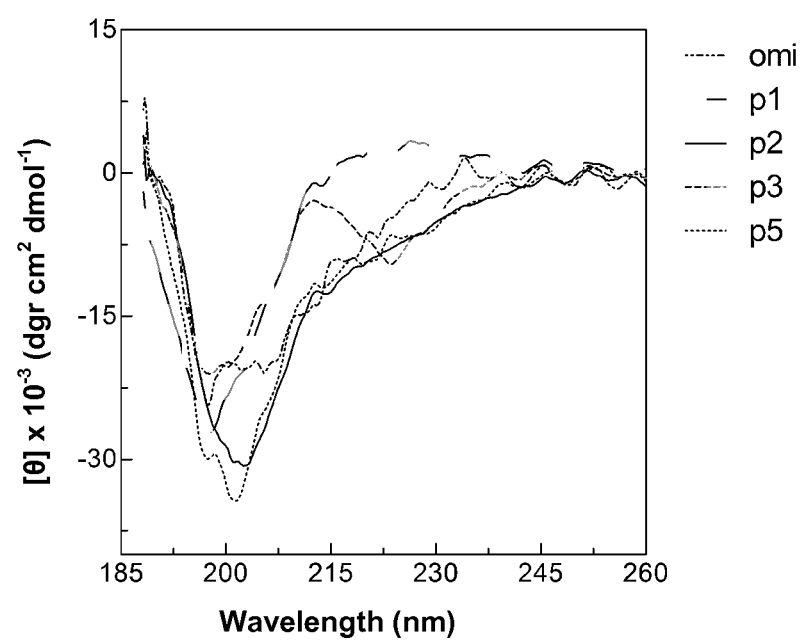
FIG. 1 shows circular dichroism (CD) spectra of the peptides of the invention in an aqueous solution; wherein it is shown that the peptides are not structured in aqueous buffer, and with a characteristic minimum at approximately 200 nm. Omi: Omiganan peptide, p1: peptide 1; p2: peptide 2, p3: peptide 3, p4: peptide 4, p5: peptide 5.

The fundamental characteristic of the peptides of the invention is their sequence and the amino acids assembly within the peptide chain which has been designed with the aim of enhancing selectivity of action over the bacterial strains, decreasing its potential cytotoxic action, which is very common in these types of peptides.

The peptides disclosed herein are active against Gram positive and Gram negative bacteria, including several types of *Staphilococcus* and *Pseudomonas*. The MIC values (minimum inhibitory concentration) are especially interesting in some strains. New synthetic peptides are disclosed in the present invention which are amidated or not amidated at the C-terminal end, and which have bactericidal activity in strains relevant for clinical issues and are resistant to traditional antibiotics. These peptides may be incorporated in a suitable vehicle for application, for instance, topically, which would provide a correct solution to the problem of superficial wounds with a high risk of infection. Additionally, they are easy to apply products and have a wide bactericidal spectrum, which solves the increasing problem of multiresistant bacterial strains.

Five peptides were synthesized having antibacterial activity, in a preferred embodiment the peptides were the following:

```
peptide 1:
                                        (SEQ ID NO: 1)
WPKWWKWKRRWGRKKAKKRRG peptide 2:
                                        (SEQ ID NO: 2)
GLLKKWLKKWKEFKRIVGY peptide 3:
                                        (SEQ ID NO: 3)
FGKEKKAWWRRRKWLK peptide 4:
                                        (SEQ ID NO: 4)
TTCDLLSGVGLPNVPQPLHCVFRGNRKIKW peptide 5:
                                        (SEQ ID NO: 5)
RIVQRIKKWLLKWKKLGY known peptide (Omiganan):
                                        (SEQ ID NO: 6)
ILRWPWWPWRRK.
```

The 5 designed and synthesized peptides of the invention, plus omiganan (peptide of the state of the art) were evaluated for their antimicrobial capacity in microdilution assays for determining the minimum inhibitory concentration (MIC). A first panel of 8 representative strains was analyzed in these assays, encompassing Gram positive and Gram negative bacteria. The results of the obtained MIC are outlined in Table 1, expressed as μg/ml of each peptide. The lowest MIC values indicate a higher antimicrobial potency.

TABLE 1

| Organism | OMI | peptide 1 | peptide 2 | peptide 3 | peptide 4 | peptide 5 |
|---|---|---|---|---|---|---|
| *Staphylococcus warneri* M6823 | 4 | 4 | 8 | 8 | >256 | 4 |
| *Staphylococcus cohnii* M6767 | 8 | 8 | 8 | 4 | >256 | 4 |

TABLE 1-continued

| Organism | OMI | peptide 1 | peptide 2 | peptide 3 | peptide 4 | peptide 5 |
|---|---|---|---|---|---|---|
| Staphylococcus aureus ATCC29213 | 16 | 16 | 64 | 128 | >256 | 16 |
| Escherichia coli ATCC25922 | 32 | 32 | 16 | 64 | >256 | 4 |
| Staphylococcus aureus M6794 | 16 | 8 | 32 | 128 | >256 | 4 |
| Pseudomonas aeruginosa ATCC27853 | 32 | 16 | 16 | 128 | >256 | 8 |
| Pseudomonas aeruginosa M13513 | 64 | 16 | 32 | 128 | >256 | 8 |
| Klebsiella pneumoniae M13540 | 64 | >128 | 16 | 128 | >256 | 8 |

Subsequently, the capacity of the peptides of the invention for lysing human erythrocytes was evaluated, as a measure of their cytotoxicity (Table 2). The assays were carried out according to the Examples and are expressed as a percentage of total lysis obtained with either water or the surfactant Tween 20. In this assays, the lower hemolysis percentage, the lower expected cytotoxic activity.

TABLE 2

| Sample | Concentration | OD 540 nm | Hemolysis % (1% Tween20) | Hemolysis % (water) |
|---|---|---|---|---|
| peptide 1 | 128 ug/ml | 0.067 | 4 | 3.4 |
| peptide 2 | 128 ug/ml | 0.641 | 46.3 | 39.8 |
| peptide 3 | 128 ug/ml | 0.036 | 1.7 | 1.5 |
| peptide 4 | 128 ug/ml | 0.04 | 2 | 1.72 |
| peptide 5 | 128 ug/ml | 0.163 | 11.1 | 9.5 |
| Omiganan | 128 ug/ml | 0.171 | 11.6 | 10 |
| Tween20 | 1% | 1.37 | 100 | 86 |
| PBS | — | 0.013 | 0 | 0 |
| water | — | 1.59 | 116.2 | 100 |

As can be seen, peptides 1, 2 and 5 have higher antimicrobial potency values. The hemolysis values are lower or similar to those of the Omiganan peptide. Even though peptide 2 has high hemolysis values, it was decided to go on with its analysis since in an eventual topical use these values would not be an impediment. In a preferred embodiment, peptides 1 and 5 are selected, which have the highest therapeutic index values, understood as the value indicating the antimicrobial potency over the cytotoxicity percentage.

Subsequently, an analysis of a panel of clinical isolates including strains with different resistance mechanisms against conventional antibiotics was carried out, all of which are of clinical relevance. In Tables 3 and 4 the results obtained when analyzing MIC of the selected peptides 1, 2 and 5, are shown, plus the control peptide Omiganan. In Table 3 the results for a panel of Gram negative bacteria are shown, and in Table 4 for a panel of Gram negative bacteria. In these tables the detected gene/s responsible for the resistance against antibiotics for each strain, are included.

In this studies, it may be seen that peptide 5 is up to eight times more active than the known peptide Omiganan in *Pseudomona aeruginosa*. A similar thing is observed with *Klebsiella pneumoniae*, where great improvements in potency of the peptides 2 and 5 are observed, while peptide 1 has a lower activity than the Omiganan peptide for that strain.

TABLES 3 and 4

| | | | MIC (ug/ml) | | | |
|---|---|---|---|---|---|---|
| Strain | ID No. | Resistance Gene | Omiganan | peptide 1 | peptide 2 | peptide 5 |
| *Pseudomonas aeruginosa* (n = 12) | | | | | | |
| P. aeruginosa | M13513 | kpc | 256 | 32 | 64 | 64 |
| P. aeruginosa | M11005 | kpc | 512 | 64 | 64 | 128 |
| P. aeruginosa | M7723 | kpc | 256 | 64 | 64 | 32 |
| P. aeruginosa | M7728 | imp | 512 | 128 | 64 | 64 |
| P. aeruginosa | M5109 | vim | 256 | 128 | 64 | 64 |
| P. aeruginosa | M5200 | vim + ges | 512 | 64 | 64 | 64 |
| P. aeruginosa | M7525 | spm | 512 | 64 | 64 | 64 |
| P. aeruginosa | M7712 | spm | 512 | 64 | 64 | 64 |
| P. aeruginosa | M5470 | ND[1] | 512 | 128 | 64 | 64 |
| P. aeruginosa | M7907 | per | 128 | 128 | 64 | 64 |
| P. aeruginosa | COS 12p | ND. | 512 | 64 | 64 | 64 |
| P. aeruginosa | ATCC 27853 | WT | 256 | | 64 | 64 |
| *Acinetobacter sp.* (n = 10) | | | | | | |
| A. baumanii | M13523 | oxa-51 | 64 | 64 | 32 | 4 |
| A. baumanii | FAV-1 | per + oxa-51 + oxa-58 | 64 | 64 | 16 | 16 |
| A. baumanii | M5179 | oxa-51 | 64 | 64 | 32 | 32 |
| A. baumanii | M7978 | imp | 64 | 64 | 16 | 8 |
| A. junii | M9013 | oxa-51 + imp | 64 | 32 | 32 | 8 |
| A. baumanii | M5277 | per | 32 | 64 | 32 | 8 |
| A. baumanii | M5949 | oxa-23 + oxa-GVI | 128 | 256 | 32 | 16 |
| A. baumanii | M7489 | oxa-51 + tem | 32 | 64 | 8 | 16 |
| A. baumanii | M9665 | oxa-51 | 64 | 128 | 4 | 32 |
| A. baumanii | M5282 | oxa-51 | 16 | 64 | 8 | 8 |
| *Klebsiella pneumoniae* (n = 12) | | | | | | |
| K. pneumoniae | M5825 | ges-3 + ctx-m-2 | 64 | >1024 | 8 | 32 |
| K. pneumoniae | M7647 | vim-like + ctx-m-2 + tem-1 + shv-1 | 1024 | >1024 | 32 | 32 |
| K. pneumoniae | M13540 | kpc | 256 | >1024 | 16 | 64 |
| K. Pneumoniae | M9885 | kpc | 256 | >1024 | 64 | 32 |

TABLES 3 and 4-continued

| Strain | ID No. | Resistance gene | | | | |
|---|---|---|---|---|---|---|
| K. Pneumoniae | M11245 | kpc + per-2 | 32 | 1024 | 16 | 8 |
| K. pneumoniae | M1803 | ctx-m-2 + per-2 + tem-1 + shv + oxa-9 | 1024 | >1024 | 32 | 64 |
| K. pneumoniae | M9140 | cit | 64 | 1024 | 32 | 32 |
| K. pneumoniae | M9310 | ctx-m-2 + shv-1 + tem-1 | 64 | >1024 | 16 | 32 |
| K. pneumoniae | M9375 | ctx-m-2 + shv-1 + tem-1 | 32 | 1024 | 64 | 16 |
| K. pneumoniae | M9170 | oxa-GIII | 128 | >1024 | 32 | 64 |
| K. pneumoniae | M9491 | mox | 128 | 1024 | 64 | 64 |
| K. pneumoniae | FAV3 | WT | 128 | 1024 | 128 | 128 |
| *Escherichia coli* (n = 9) | | | | | | |
| E. coli | Cos15 | per + tem | 64 | 128 | 64 | 64 |
| E. coli | M9884 | WT | 64 | 128 | 32 | 32 |
| E. coli | M9209 | kpc | 64 | 128 | 64 | 128 |
| E. coli | M7859 | cit | 64 | 128 | 32 | 16 |
| E. coli | NEU23 | oxa-GIII + tem | 32 | 128 | 32 | 32 |
| E. coli | ABC11 | ctx-m-2 | 64 | 128 | 32 | 32 |
| E. coli | LCA1 | ctx-m-2 + tem-1 | 64 | 128 | 64 | 64 |
| E. coli | M5306 | ctx-m-2 + tem-1 + per-2 | 64 | 128 | 4 | 64 |
| E. coli | ATCC 25922 | WT | 64 | 256 | 32 | 32 |

| | | | MIC (ug/ml) | | | |
|---|---|---|---|---|---|---|
| Strain | ID No. | Resistance gene | Omiganan | peptide 1 | peptide 2 | peptide 5 |
| *Staphylococcus aureus* (n = 11) | | | | | | |
| S. aureus | ATCC29213 | WT | 32 | 32 | 64 | 32 |
| S. aureus | M6794 | mecA | 64 | 32 | 64 | 64 |
| S. aureus | 204 | ermA | 64 | 64 | 64 | 32 |
| S. aureus | 28 | ermA | 32 | 32 | 64 | 64 |
| S. aureus | 33 | msrA | 32 | 32 | 128 | 64 |
| S. aureus | 239 | ermC | 32 | 32 | 64 | 64 |
| S. aureus | M6276 | ermA + lnuA | 32 | 16 | 128 | 64 |
| S. aureus | M2832 | mecA | 64 | 32 | 128 | 64 |
| S. aureus | M4046 | mecA | 32 | 32 | 128 | 32 |
| S. aureus | M6820 | mecA | 128 | 64 | 128 | 64 |
| S. aureus | M6784 | mecA | 32 | 32 | 32 | 32 |
| Coagulase Negative *Staphylococcus* (CNS) (n = 12) | | | | | | |
| S. epidermidis | M2919 | mecA | 8 | 16 | 16 | 8 |
| S. epidermidis | M2921 | mecA | 8 | 8 | 8 | 8 |
| S. saprophyticus | M4070 | mecA | 8 | 16 | 32 | 8 |
| S. saprophyticus | M2981 | mecA | 8 | 16 | 8 | 8 |
| S. epidermidis | M2923 | WT | 8 | 16 | 16 | 16 |
| S. epidermidis | M2931 | WT | 16 | 16 | 16 | 8 |
| S. haemolyticus | M2976 | mecA | 4 | 16 | 8 | 8 |
| S. haemolyticus | M3014 | WT | 4 | 16 | 8 | 8 |
| S. hominis | M2973 | mecA | 4 | 4 | 4 | 4 |
| S. hominis | M2967 | mecA | 4 | 8 | 8 | 8 |
| S. warnerii | M6823 | mecA | 8 | 8 | 8 | 8 |
| S. cohnii | M6767 | mecA | 4 | 16 | 16 | 8 |
| *Enterococcus* spp. (n = 17) | | | | | | |
| E. faecium | M2304 | vanA | 4 | 16 | 16 | 8 |
| E. faecium | M2664 | vanA | 8 | 16 | 8 | 8 |
| E. faecium | M2619 | vanB | 16 | 32 | 16 | 16 |
| E. faecium | M2481 | vanB | 16 | 32 | 16 | 16 |
| E. faecium | ZAP95 | WT | 16 | 32 | 16 | 16 |
| E. faecium | M6261 | N.D | 16 | 32 | 16 | 16 |
| E. faecalis | M4899 | vanB | 256 | 256 | 128 | 256 |
| E. faecalis | M6534 | vanB | 256 | 128 | 256 | 256 |
| E. faecalis | M4992 | vanA | 128 | 128 | 128 | 128 |
| E. faecalis | M6383 | vanA | 128 | 128 | 128 | 128 |
| E. faecalis | M4449 | vanA | 128 | 128 | 128 | 128 |
| E. faecalis | ATCC 51299 | vanB | 256 | 256 | 256 | 256 |
| E. faecalis | ATCC 29212 | WT | 128 | 64 | 128 | 128 |
| E. faecalis | M6983 | vanA | 128 | 64 | 128 | 128 |
| E. gallinarum | M2723 | vanC1 + vanA | 16 | 32 | 32 | 16 |
| E. gallinarum | M2685 | vanC1 + vanA | 16 | 16 | 16 | 16 |
| E. raffinosus | M6187 | vanA | 4 | ND | 8 | 8 |

In order to evaluate the structure that the peptides acquire in aqueous solution and in the presence of a surfactant such as SDS, a circular dichroism (CD) assay was performed. This way, the differences between the structured acquired by the peptides and their biological activity could be correlated.

Figure 2:
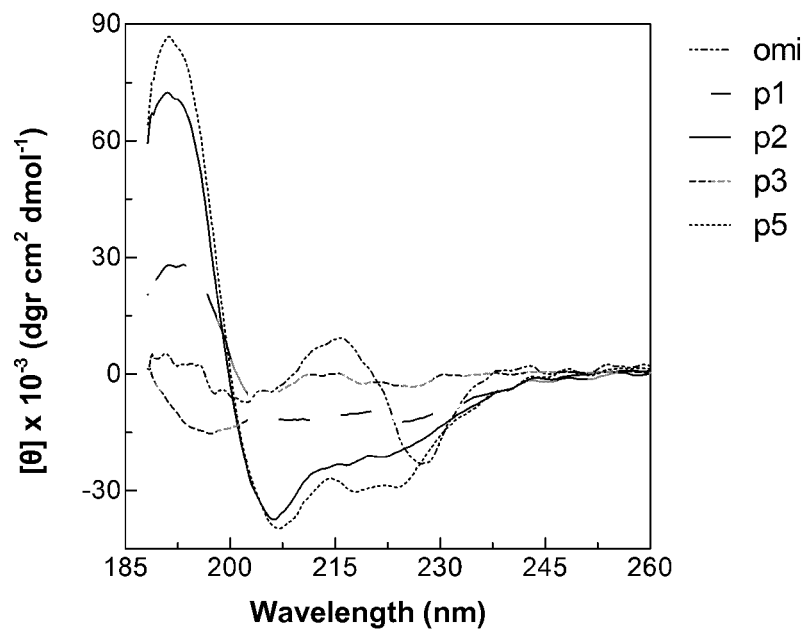
FIG. 2 shows circular dichroism (CD) spectra of the peptides of the invention in a solution with SDS, wherein conformational changes are observed in the peptides 1, 2 and 5, which are consistent with the formation of alpha-helix structures. Omi: Omiganan peptide, p1: peptide 1; p2: peptide 2, p3: peptide 3, p4: peptide 4, p5: peptide 5.

The CD spectra of the peptides in aqueous solution show that said peptides are not structured in aqueous buffer, with a characteristic minimum at approximately 200 nm. With the addition of SDS micelles, conformational changes are generated in peptides 2 and 5, which are consistent with the formation of alpha-helix structures, with two characteristic minimums, close to 208 and 222 nm. Peptide 1 is also subjected to a similar transition, however the structure level acquired is much lower than that observed in peptides 2 and 5. The CD spectrum of peptide 3 is almost invariable with the addition of SDS micelles, indicating the persistence of a disorganized conformation. In the case of Omiganan, the spectrum is significantly modified in the presence of SDS, with the band at 200 nm diminishing and a new band appearing near 230 nm, which may be a result of the interaction between side chains in tryptophan (FIGS. 1 and 2). These experimental results match the theoretical parameters obtained by computational analysis.

Physical-chemical parameters of the peptides theoretically analyzed for each sequence are summarized in Table 5.

TABLE 5

|  | peptide 1 | peptide 2 | peptide 3 | peptide 4 | peptide 5 |
|---|---|---|---|---|---|
| Isoelectric point | 13.10 | 10.89 | 12.25 | 9.85 | 11.75 |
| Net charge | +12 | +6 | +7 | +3 | +7 |
| Hydrophobicity * | +29.04 | +20.51 | +23.38 | +19.05 | +16.10 |
| Alpha-helix content ** | 1.03 | 5.35 | 1.54 | 0.11 | 7.07 |

* Wimley-White Scale Kcal mol$^{-1}$
** According to AGADIR algorithm

When the non-amidated peptides of the invention were assessed the results shown in Table 6 were obtained.

TABLE 6

NON-AMIDATED PEPTIDES, MIC (µg/ml) IN AGAR DILUTION

| Species | ID No. | Resistance Gene | Omiganan | peptide 1 | peptide 2 | peptide 3 | peptide 4 | peptide 5 |
|---|---|---|---|---|---|---|---|---|
| S. warnerii | M6823 | Oxa-R | 16 | 16 | 8 | 32 | >128 | 8 |
| S. cohnii | M6767 | mecA | 16 | 16 | 16 | 32 | >128 | 8 |
| S. aureus | M6794 | MRSA | >128 | >128 | >128 | >128 | >128 | >128 |
| E. coli | ATCC 25922 | WT | >128 | >128 | 128 | >128 | >128 | 64 |
| S. aureus | ATCC29213 | MSSA | >128 | >128 | >128 | >128 | >128 | >128 |
| P. aeruginosa | ATCC 27853 | WT | >128 | >128 | >128 | >128 | >128 | >128 |
| P. aeruginosa | M13513 | KPC | >128 | >128 | >128 | >128 | >128 | >128 |
| K. pneumoniae | M13540 | KPC | >128 | >128 | 64 | >128 | >128 | >128 |

For the concentrations studied: peptide 1 has activity against *S. warnerii* and *S. cohnii*; peptide 2 has activity against *S. warnerii, S. cohnii, E. coli* and *K. pneumoniae*, peptide 3 has activity against *S. warnerii* and *S. cohnii*, peptide 4 does not have activity against any of the tested strains and peptide 5 has activity against *S. warnerii, S. cohnii* and *E. coli*.

The present invention is better illustrated with the following examples, which are not to be construed as a limitation to the scope thereof. On the contrary, it must be clearly understood that other embodiments, modifications and equivalents thereof may be apparent for a person skilled in the art, after reading the present description without departing from the spirit of the present invention and/or scope of the annexed claims.

EXAMPLES

The design of the peptides was aimed at generating amphipathic, cationic sequences, of the alpha-helix type. To this end, multiple alignment informatics tools, simulators of physical-chemical properties such as hydrophobicity or alpha-helix content, were used. All of said informatics software (BLAST, CLUSTAL, AGADIR, ExPASY) are freeware and available through the Internet.

In this analysis, the sequences and amino acids were set forth in specific consensus positions, when available, or semiconserved motifs in some known peptides. Taking into consideration these diverse parameters, five in silico peptides were designed, having between 18 and 30 amino acids (SEQ ID NOs: 1-5).

Synthesis and Purification

The peptide synthesis was carried out by means of automated SPPS (solid phase peptide synthesis) synthesis and subsequently analyzed by mass spectrometry and purified by reverse phase HPLC.

Also, each peptide was amidated in the C-terminal end.

Circular Dichroism Analysis

Far-UV Circular Dichroism

Secondary structure content was studied by far-UV Circular dichroism spectroscopy, using a JASCO J 810 equipment (Jasco Corp., Tokio, Japan) calibrated with (+)10-camphorsulfonic acid. Measurements were carried out under a 8 l/h-nitrogen gas flux, at a temperature of 20° C., controlled by a Peltier-type system (JASCO).

Spectra between 185 and 320 nm were recorded, using a 0.1 cm-optical path cell. Concentration of the peptides were 40 µM, dissolved in 10 mM sodium phosphate buffer pH 7.0, or in the same buffer with 10 mM sodium dodecyl sulfate (SDS). Sensitivity was 100 millidegrees. Scan speed was 50 nm/min, a response time of 1 s and a bandwidth of 1 nm. An average of five spectra was performed for each sample. The average was corrected by buffer absorption and then baselined to zero using the average of readings at 290 and 320 nm. Finally, the data were smoothed using a Golay polynomial Savizky fourth grade, with a window of ten points. The spectra were converted to mean molar ellipticity per residue by using the equation: $[\theta]=\theta/(10 \times c \times n \times d)$ wherein $[\theta]$ is the molar ellipticity (in degrees×cm$^2$×dmol$^{-1}$), $\theta$ is the ellipticity in millidegrees, n is the number of residues in the peptide and c its molar concentration, d the length of the cell in centimeters.

In vitro sensitivity assay of aerobically growing bacteria, using the disc diffusion method was performed according to the standards in the M2 document of the CLSI (*Clinical and*

Laboratory Standards Institute: Performance Standards for Antimicrobial Disk Susceptibility Tests.) using the non-amidated peptides In brief, intermediate solutions (10×) of the antimicrobial non-amidated peptides were prepared by serial dilutions 1:2, 1:4 and 1:8 by two-fold dilutions. Then, one part of the solution of the antimicrobial peptide 10× was added to nine parts of melted bacteriological agar. The antibiotic solution was added for each dilution, in the melted agar and cooled to 45-50° C. in a water bath. Then, the agar-antibiotic mixture was placed in a Petri dish until a 3-4 mm depth was reached. The inoculum is prepared with a turbidity of 0.5 in the McFarland scale (approximately 1-2 $10^8$ CFU/ml). The final inoculum required for the agar dilution test is $10^4$ colony forming units (CFU) per "spot" having 5-8 mm in diameter. The inoculated plates must be incubated upside down at 35° C. for a period of 16-20 hs. MIC was recorded as the value of the lower dilution completely inhibiting bacterial development, without considering the development of a single colony or a slight film caused by the inoculum deposit. The final point in these cases will correspond to the concentration at which there is more than 80% reduction in growth as compared with the control.

Analysis of Antimicrobial Activity

Antimicrobial activity was analyzed by means of the determination of the MIC (minimum inhibitory concentration) by the microdilution technique. The technique was carried out in the standard fashion according to (CLSI M07-A9 Vol. 32 No 2. January 2012). The peptide concentration range used was from 0.5 μg/mL to 512 μg/mL in two-fold serial dilutions. The used medium was MH Difco broth supplemented with cations, at a final concentration of $Ca^{++}$ 20-25 mg/L and $Mg^{++}$ 10-12.5 mg/L. The working inoculum used corresponds to a 1/100 dilution of a bacterial suspension equivalent to 0.5 in the Mc Farland scale.

Analysis of Hemolytic Activity

Evaluation of cytotoxic activity was performed by means of an erythrocyte hemolysis assay (according to *Pure Appl. Chem.*, Vol. 79, No. 4, pp. 717-728, 2007). In brief, from a volume of heparinized human whole blood, 3 times that volume of PBS is added and centrifuged 10 minutes at 1500 rpm, repeating the washing two more times. 10% blood solutions in PBS were prepared with that pellet. Subsequently, each group was added the corresponding peptide at the indicated concentration and incubated at 37° C. for 30 minutes. After incubation time, each tube was centrifuged at 10000 rpm for 5 minutes and the supernatant was read in a spectrophotometer at 600 nm.

Bacterial Strains 78 isolates were studied, previously characterized in the Reference National Laboratory INEI-ANLIS of the Instituto Carlos Malbrán, with different antibiotic resistance mechanisms.

40 Gram positive strains, 37 INEI-ANLIS isolates were analyzed plus three ATCC reference strains:

*Staphylococcus aureus* (11 isolates)
*Staphylococcus* Coagulase Negative (12 isolates: 4 *S. epidermidis*, 2 *S. saprophyticus*, 2 *S. haemolyticus*, 2 *S. hominis*, 1 *S. warnerii*, 1 *S. cohnii*)
*Enterococcus* spp. (17 isolates: 6 *E. faecium*, 8 *E. faecalis*, 2 *E. gallinarum*, 1 *E. raffinosus*)

The resistance mechanisms for this group, as may be seen in Table 4, were as follows: WT, vanA, vanB, vanC, mecA, ermA, ermC, msrA, InuA.

43 Gram negative strains, 41 INEI-ANLIS isolates, plus three reference ATCC strains were analyzed:

*Pseudomonas aeruginosa* (12 isolates)
*Acinetobacter* sp. (10 isolates: 9 *A. baumanii*, 1 *A. junii*)
*Klebsiella pneumoniae* (12 isolates)
*Escherichia coli* (9 isolates)

The resistance mechanisms for this group, as may be seen in Table 4, were as follows: (tem-1, cmy, cit, shv-1, ctx-m-2, per-2, ges-1/3, veb-1, oxa-9, oxa-23, oxa-58, vim-11, imp-1/13/16, spm-1, kpc-2).

---

The invention claimed is:

1. An antimicrobial peptide comprising an amino acid sequence selected from the group consisting of SEQ ID NOs: 1-5.

2. The peptide according to claim 1, wherein the peptide is amidated at the C-terminal end.

3. A bactericidal composition comprising an effective amount of at least one peptide according to claim 1 and excipients.

4. The bactericidal composition according to claim 3, wherein said bacterial composition comprises an amount between 0.5 μg/mL and 1024 μg/mL of the peptides.

5. The bacterial composition according to claim 3, wherein the peptide is amidated at the C-terminal end.

6. A method for treating a Gram positive or Gram negative bacterial infection comprising administering an effective amount of a peptide comprising an amino acid sequence selected from the group consisting of SEQ ID NOs: 1-5 to an animal in need thereof.

7. The method according to claim 6, wherein the Gram positive bacterial infection is selected from the group consisting of *Staphylococcus aureus, Staphylococcus epidermidis, Staphylococcus saprophyticus, Staphylococcus haemolyticus, Staphylococcus hominis, Staphylococcus warnerii, Staphylococcus cohnii, Enterococcus faecium, Enterococcus faecalis, Enterococcus gallinarum* and *Enterococcus raffinosus*.

8. The method according to claim 6, wherein the Gram negative bacterial infection is selected from the group consisting of *Pseudomonas aeruginosa, Acinetobacter baumanii, Acinetobacter junii, Klebsiella pneumoniae* and *Escherichia coli*.

* * * * *

SEQUENCE LISTING

<160> NUMBER OF SEQ ID NOS: 6

<210> SEQ ID NO 1
<211> LENGTH: 21
<212> TYPE: PRT
<213> ORGANISM: Artificial Sequence
<220> FEATURE:
<223> OTHER INFORMATION: peptide 1

<400> SEQUENCE: 1

Trp Pro Lys Trp Trp Lys Trp Lys Arg Arg Trp Gly Arg Lys Lys Ala
1               5                   10                  15

Lys Lys Arg Arg Gly
            20

<210> SEQ ID NO 2
<211> LENGTH: 19
<212> TYPE: PRT
<213> ORGANISM: Artificial Sequence
<220> FEATURE:
<223> OTHER INFORMATION: peptide 2

<400> SEQUENCE: 2

Gly Leu Leu Lys Lys Trp Leu Lys Lys Trp Lys Glu Phe Lys Arg Ile
1               5                   10                  15

Val Gly Tyr

```
<210> SEQ ID NO 3
<211> LENGTH: 16
<212> TYPE: PRT
<213> ORGANISM: Artificial Sequence
<220> FEATURE:
<223> OTHER INFORMATION: peptide 3

<400> SEQUENCE: 3

Phe Gly Lys Glu Lys Lys Ala Trp Trp Arg Arg Arg Lys Trp Leu Lys
1               5                   10                  15

<210> SEQ ID NO 4
<211> LENGTH: 30
<212> TYPE: PRT
<213> ORGANISM: Artificial Sequence
<220> FEATURE:
<223> OTHER INFORMATION: peptide 4

<400> SEQUENCE: 4

Thr Thr Cys Asp Leu Leu Ser Gly Val Gly Leu Pro Asn Val Pro Gln
1               5                   10                  15

Pro Leu His Cys Val Phe Arg Gly Asn Arg Lys Ile Lys Trp
            20                  25                  30

<210> SEQ ID NO 5
<211> LENGTH: 18
<212> TYPE: PRT
<213> ORGANISM: Artificial Sequence
<220> FEATURE:
<223> OTHER INFORMATION: peptide 5

<400> SEQUENCE: 5

Arg Ile Val Gln Arg Ile Lys Lys Trp Leu Leu Lys Trp Lys Lys Leu
1               5                   10                  15

Gly Tyr

<210> SEQ ID NO 6
<211> LENGTH: 12
<212> TYPE: PRT
<213> ORGANISM: Artificial Sequence
<220> FEATURE:
<223> OTHER INFORMATION: Omiganan

<400> SEQUENCE: 6

Ile Leu Arg Trp Pro Trp Trp Pro Trp Arg Arg Lys
1               5                   10
```